United States Patent
Llewelyn

(10) Patent No.: US 12,279,873 B2
(45) Date of Patent: Apr. 22, 2025

(54) COLOR AND SYMBOL CODED DISPLAY ON A DIGITAL BADGE FOR COMMUNICATING PERMISSION TO APPROACH AND ACTIVATE FURTHER DIGITAL CONTENT INTERACTION

(71) Applicant: Blue Storm Media Inc, Yedwood city, CA (US)

(72) Inventor: Gareth Llewelyn, Berks (GB)

( * ) Notice: Subject to any disclaimer, the term of this patent is extended or adjusted under 35 U.S.C. 154(b) by 163 days.

(21) Appl. No.: 18/144,190

(22) Filed: May 6, 2023

(65) Prior Publication Data
US 2023/0360503 A1 Nov. 9, 2023

Related U.S. Application Data

(63) Continuation of application No. 17/358,499, filed on Jun. 25, 2021, which is a continuation-in-part of (Continued)

(51) Int. Cl.
*A61B 5/256* (2021.01)
*A61B 5/00* (2006.01)
(Continued)

(52) U.S. Cl.
CPC ............ *A61B 5/256* (2021.01); *A61B 5/0062* (2013.01); *A61B 5/165* (2013.01); *A61B 5/41* (2013.01); *A61B 5/4803* (2013.01); *A61K 9/0019* (2013.01); *A61K 9/5115* (2013.01); *G01N 33/54326* (2013.01); *G01N 33/54346* (2013.01); *G06F 1/163* (2013.01); *G06F 3/011* (2013.01); *G06F 3/14* (2013.01); *G06K 19/06028* (2013.01); *G06K 19/0723* (2013.01); (Continued)

(58) Field of Classification Search
CPC . A61B 5/256; G06F 1/163; G06F 3/14; G06F 3/147; G06K 19/0723; G06Q 50/01; H04W 4/80; H04W 4/206
See application file for complete search history.

(56) References Cited

U.S. PATENT DOCUMENTS 9,721,147 B1 * 8/2017 Kapczynski ......... G06Q 50/265
10,237,256 B1 * 3/2019 Pena ................... H04L 63/0853
(Continued)

*Primary Examiner* — Vernal U Brown
(74) *Attorney, Agent, or Firm* — Mohamed C. Azeez

(57) ABSTRACT

The method involves using a digital badge device worn on the chest of a user to visually convey personal attributes to others in line of sight. It begins by configuring the badge device to communicate wirelessly with the user's mobile device. Next, a personal attribute of the user is determined based on input from the user or device-captured data. This attribute could relate to the user's affiliation, emotional state, physical activity, and more. Finally, a pre-defined color and/or symbol code representing the determined attribute is displayed on the badge device's screen for others to see. This provides an easily interpretable visual cue to communicate specific personal attributes to different users. By employing this method, the badge wearer can convey information about themselves without the need for verbal communication. The method offers a convenient and efficient way to signal personal attributes in situations where direct interaction may be limited or impractical.

20 Claims, 13 Drawing Sheets

Related U.S. Application Data application No. 17/211,099, filed on Mar. 24, 2021, now Pat. No. 11,562,815, which is a continuation-in-part of application No. 17/154,162, filed on Jan. 21, 2021, now Pat. No. 11,574,715, which is a continuation-in-part of application No. 16/867,413, filed on May 5, 2020, now Pat. No. 11,423,755, which is a continuation-in-part of application No. 15/645,891, filed on Jul. 10, 2017, now Pat. No. 10,783,546, application No. 18/144,190 is a continuation of application No. 15/409,460, filed on Jan. 18, 2017, now abandoned.

(60) Provisional application No. 62/603,163, filed on May 17, 2017.

(51) Int. Cl.

| | | |
|---|---|---|
| *A61B 5/16* | (2006.01) | |
| *A61K 9/00* | (2006.01) | |
| *A61K 9/51* | (2006.01) | |
| *G01N 33/543* | (2006.01) | |
| *G06F 1/16* | (2006.01) | |
| *G06F 3/01* | (2006.01) | |
| *G06F 3/14* | (2006.01) | |
| *G06K 19/06* | (2006.01) | |
| *G06K 19/07* | (2006.01) | |
| *G06Q 30/0251* | (2023.01) | |
| *G06Q 30/0279* | (2023.01) | |
| *G06Q 50/00* | (2012.01) | |
| *G08B 5/36* | (2006.01) | |
| *G16H 10/60* | (2018.01) | |
| *G16H 40/67* | (2018.01) | |
| *G16H 50/00* | (2018.01) | |
| *G16H 50/20* | (2018.01) | |
| *H04W 4/23* | (2018.01) | |
| *H04W 4/80* | (2018.01) | |
| *B82Y 5/00* | (2011.01) | |
| *B82Y 25/00* | (2011.01) | |
| *B82Y 30/00* | (2011.01) | |
| *B82Y 40/00* | (2011.01) | |
| *H01F 1/03* | (2006.01) | |

(52) U.S. Cl.
CPC ..... *G06Q 30/0267* (2013.01); *G06Q 30/0279* (2013.01); *G06Q 50/01* (2013.01); *G08B 5/36* (2013.01); *G16H 10/60* (2018.01); *G16H 40/67* (2018.01); *G16H 50/00* (2018.01); *G16H 50/20* (2018.01); *H04W 4/23* (2018.02); *H04W 4/80* (2018.02); *B82Y 5/00* (2013.01); *B82Y 25/00* (2013.01); *B82Y 30/00* (2013.01); *B82Y 40/00* (2013.01); *H01F 1/0313* (2013.01)

(56) References Cited

U.S. PATENT DOCUMENTS

2008/0169350 A1* 7/2008 Audebert ........... G06Q 20/4014
　　　　　　　　　　　　　　　　　　　　235/492
2015/0348498 A1* 12/2015 Anderson ............... G06F 3/147
　　　　　　　　　　　　　　　　　　　　345/520

* cited by examiner

COLOR AND SYMBOL CODED DISPLAY ON A DIGITAL BADGE FOR COMMUNICATING PERMISSION TO APPROACH AND ACTIVATE FURTHER DIGITAL CONTENT INTERACTION

FIELD OF INVENTION

The present invention relates to an interactive digital badge, and more particularly, relates to a symbol and, or color-coded display cue and protocol for communicating between badge wearers a permission to approach and to further activate a digital interaction. Additionally, the invention pertains generally to the field of interactive wearable badges or other devices for applications such marketing and advertising, and more particularly to interactive marketing using wireless protocol e.g., Bluetooth, as well as colors, social media accounts, barcodes, and mutual action between consumers, badges, marketers, as well as services, for example, using content management systems.

BACKGROUND OF INVENTION

Badges have long been a mainstay in public gathering situations as a way to identify the people engaged in the public gathering. It has also been a primary way of communicating to others a level of credential to facilitate access or a professional process. While the badge has long been simply a name card, with title, and possibly a photo, they have recently morphed into digital versions. Digital badges may be operatively coupled to networked devices and be enabled to reconfigurably display items. According to one embodiment disclosed and claimed by Identity Systems, Inc. (US20150348498), the digital badge device may include a mounting means, power source, microprocessor, memory, and display to receive and display digital content from a network device according to a pre-defined rule. Identity Systems badge may be associated with an individual or employee, and then automatically display at least the name of the individual or employee based on the association and the pre-defined interaction rules between the digital badge and networked device.

Identity Systems digital badge does not disclose or claim for any digital interaction between digital badges. In other words, the badges are not configured to communicate between badges or share digital content between badges or from badge to networked device. Therefore, the badges are simply contemplated as being a visual display of identity or group/brand association that may be dynamically displayed according to a pre-defined rule. However, it is not envisioned to serve as a true digital communication tool, that may interact with other badges, and push digital content from one badge to another badge in a dynamic and targeted fashion. Additionally, badge-displayed content or badge-badge shared content is not enabled for social media sharing or inclusion into a running virtual footprint of a badge wearer. What's more, without tracking of such a virtual footprint, behavior or influence ratings cannot be accurately identified in order to dynamically push targeted content.

Aside from a lack of badge-badge or badge-device interactivity or footprint tracking for targeted content delivery, digital badges lack a system or protocol for communicating an approach or further engagement of digital content interaction. More specifically, badges, such as Invent Systems, lack a symbol or color-coded display cue between users who are in their line of 15 sight (or groups of people) for communicating a permission to approach, and more particularly, further sharing of content messages, emotions, feelings, wellbeing, states of mind, general interest, marketing and advertising, and interactive behavior for likeminded people.

Digital badges need a form of universal standard language which would transcend normal language and enhance it for the digital communication between at least two badges or at least between badge and receiver. The communication protocol would also need to take this language into account to enable humans to act on the language interaction. Conventionally, people cannot transmit a message directly to another person who is in their line of sight without talking, signaling or using a facial expression to communicate with them. There is currently no method for a person to send an electronic signal to person in their line of sight directly. There is currently no method for an individual to display and instantly transmit their willingness to be approached, feelings, emotions, state of mind, state of like-mindedness, social media footprint, general interests and digital information or online dashboards. Furthermore, there is no global standard or universal symbol language to communicate non-verbal approach messages via badge devices. Currently, there is also no way for two likeminded people to share non-verbal content messages between badges and, or static devices.

Conventionally worn badges fail to display individual data dynamically on wearable badges. Furthermore, conventional badges fail to enable individuals to interact using wearable badge via smartphones. Moreover, conventional badges fail to display dynamically changing advertisement on such wearable badges, for example, for interaction via smartphones.

Additionally, conventional badges fail to change color based on data from social media interactions or any other data; and, in particular, conventional badges fail to change color and display content managed from content management systems.

SUMMARY

The non-verbal line of sight electronic communication protocol (NVP) described herein allows the viewer to instantly understand the symbol and, or color-coded display cues of the interactive badge and understand whether the individual displaying the visual cues can be: (1) approached and (2) whether an information exchange can take place immediately or in the future. It also allows the user to send and receive information that could not previously be exchanged through normal human communication means.

Generally, the non-verbal line of sight electronic communication protocol (NVP) includes a standardized set of symbols, colors, and electronic communication protocol standards that enhance human communication to a new level. The NVP allows individuals to create new human behaviors and send messages beyond the natural senses. The NVP allows individuals to build their own window of their life, display it on a personal digital display, and then have others interact with them. The NVP allows individuals to 'think' by creating their life window, 'act' by uploading to their personal digital display, and 'do' by using the interactive communication protocol.

The NVP allows communication between humans to take place while in their line of sight over and above their normal senses. The NVP can be implemented on any personal digital display that is running the NVP protocol. This protocol allows a signal to be passed between NVP devices only when certain combination of symbols and colors are displayed. This communication can trigger the transfer of information from one individual to another. Preferably, this NVP interaction guided by the standardized set of symbols and, or colors may be displayed on a center and, or surround visual display of an interactive badge worn by a first user, and in the line of sight by at least a second user.

It is one object of the invention to disclose a non-verbal line of sight electronic communication (NVP) system, comprising an interactive badge device with a line-of-sight device visual display. The device visual display being at least one of a surround device display and, or a center device display. Additionally, the device may have an interface module housed within the interactive badge device and configured for causing an event state change between at least one of a mobile device, surround device display and, or center device display. Moreover, the system may have a processor; a non-transitory storage element coupled to the processor; and encoded instructions stored in the non-transitory storage element, wherein the encoded instructions when implemented by the processor, configure the system to: (1) upload NVP interaction rules and curated NVP content for display on any one of a first user's device based on the first user's interaction rules and scheduler criteria; (2) send at least one of an interaction and, or content message based on the first user's interaction rules and scheduler criteria to at least one of a second user's device within range and contingent on the second user's interaction rules; and (3) based on the second user's interaction rules, accept or deny the first user interaction message, and if accepted, decode a unique tag to trigger a unique digital event, wherein the digital event may be at least one of an image, video, sound, vibration, flash, signal, symbol, color, text, upload, sequence, download on any one of the user's device visual display, and, or over a network.

It is another object of the invention to disclose a non-verbal line of sight electronic communication protocol. The communication protocol comprising a non-verbal symbol language for communicating wirelessly over electronic devices, including interactive badges and, or displays, between users and, or static receivers, who are in one another's line of sight; and the symbol language displayed on the interactive badge and, or display and, or static receivers communicate whether a first user can approach at least a second user or not for further digital interaction.

It is yet another object of the invention to provide for a device-centric, non-verbal line of sight electronic communication protocol. The device-centric, non-verbal line of sight electronic communication protocol comprising a non-verbal symbol language for communicating wirelessly over electronic devices, including an interactive badge with a line-of-sight device visual display, between users who are in one another's line of sight. The symbol language further comprising a set of any shaped and, or colored symbols that are programmably displayed on the device visual display, wherein the device visual display is at least one of a surround device display and, or a center device display. Furthermore, based on the programmably displayed set of shaped and, or colored symbols on the device visual display, communicate whether a first user can approach at least a second user or not for further digital interaction.

Aspects and advantages of this invention may be realized in other applications, aside from the intended application of interactive badge device-mediated communication and a communication protocol thereof. Other pertinent applications that may exploit the aspects and advantages of this invention are: digital advertising and digital commerce platforms integrated into the NVP communication system and protocol. For instance, an activity footprint of a user's displayed NVP content and, or replicated digital or virtual NVP content may be tracked for advertisers to target the most influential users for a brand display-for-hire. Moreover, a plurality of advertisers may bid for the most influential user's using a bidding module within the advertising platform, creating upward pressure on the brand display-for-hire fees. What's more, tracking of a user's NVP line of content displayed or virtually replicated, may enable a commerce platform or participants of the platform to push suggested digital content that is personalized to the user based on the user's running NVP content. Yet another digital event that may be triggered: may be the interaction of the badge device with other badge devices or fixed-access devices near access-gates, wherein the symbol and, or color-coded display on badge or fixed-access devices invite for approach; once approached and interacted with, uploading an authentication tag over a network to a remote server; validating the authentication tag against a library of authenticated tags; downloading the validated tag and using the symbol and color-coded display on the badge device or fixed-access device to communicate permission to access. Additional digital events may include enabling the same interactive badge devices or fixed-access devices to process payment transactions, over a network, via an intermediary payment system.

Generally, interactive wearable badge includes electronic device, pair-able wirelessly with another electronic device, wherein one device changes color programmably according to user donation to charitable application. At least one device programmably may display image/video, or change color according to social media interaction. Automated system displays individualized color donation by determining individual level of donation to charity or cause, to display colors electronically showing determined level of donation. Personal attributes may be displayed by automatically designing unique color sequence corresponding to personal advocacy index, mood, medical condition, age, availability, physical movement, and/or music frequency. Wireless interaction may be configured exclusively between devices. Magnetic attachment elements include magnetic/magnetizable material to facilitate clip-able assembly, such elements configurable as interactive personal badge for displaying programmable color sequence. Preferable element may comprise flying saucer design having magnetic clip with domed glass screen.

Other aspects and advantages of the invention will be apparent from the following description and the appended claims.

BRIEF DESCRIPTION OF FIGURES

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Overview:

The present disclosure relates to a new non-verbal language that has been developed for the emerging electronic line of sight badge communication. The language will be referred to in the document as NVP which an abbreviation of Non-Verbal person to person line of sight communication protocol standard. NVP is both a language and a communication protocol and this document initially describes both and then gives examples of how this is programmed and then examples or actual uses in the identified markets.

Figure 1:
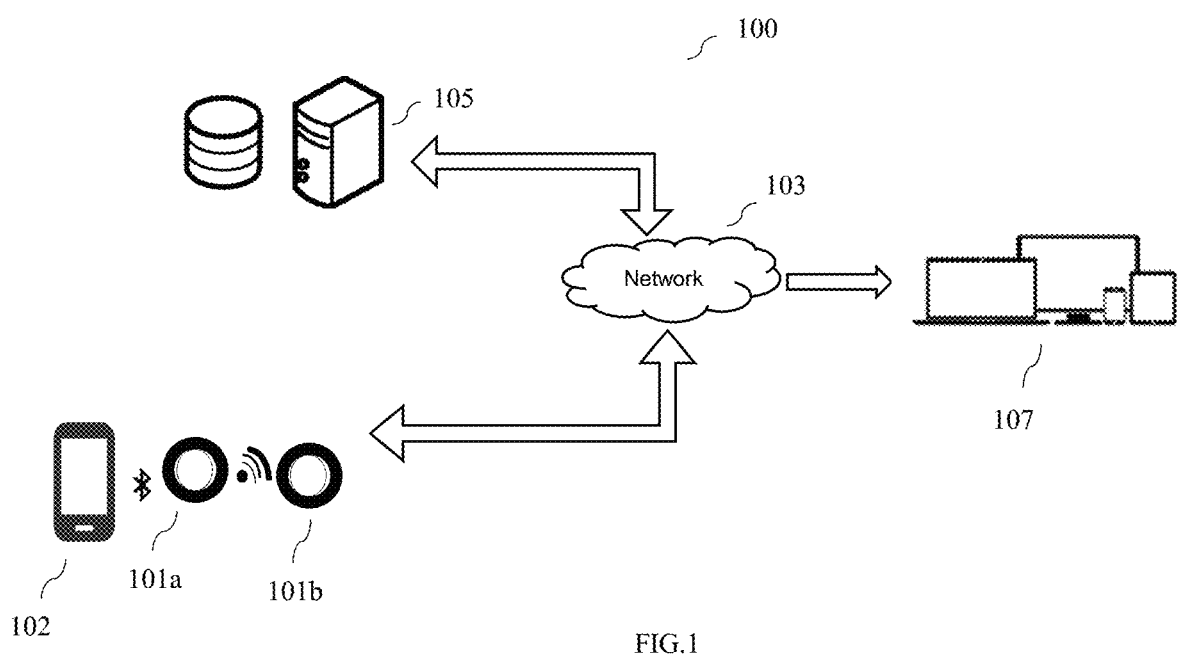
FIG. 1 illustrates a network diagram of the NVP communication system in accordance with an aspect of the invention.

Now in reference to FIG. 1. FIG. 1 illustrates an exemplary system environment 100 in which various embodiments of the non-verbal line of sight communication protocol system (NVP) can be practiced. In accordance with an exemplary embodiment, the NVP system 100 comprises: an interactive badge device 101a, 101b with a line of sight device visual display; the device visual display being at least one of a surround device display and, or a center device display; a processor; a non-transitory storage element coupled to the processor; encoded instructions stored in the non-transitory storage element, wherein the encoded instructions when implemented by the processor, configure the system 100 to: upload NVP interaction rules and curated NVP content for display on any one of a first user's interactive badge device 101a based on the first user's interaction rules and scheduler criteria; send at least one of an interaction and, or content message based on the first user's interaction rules and scheduler criteria to at least one of a second user's interactive badge device 101b within range and contingent on the second user's interaction rules; and based on the second user's interaction rules, accept or deny the first user interaction message, and if accepted, decode a unique tag to trigger a unique digital event, wherein the digital event may be at least one of an image, video, sound, vibration, flash, signal, symbol, color, text, sequence, upload, download on any one of the user's device visual display and, or over a network.

The network 103 may be any suitable wired network, wireless network, a combination of these or any other conventional network, without limiting the scope of the present invention. Few examples may include a LAN or wireless LAN connection, an Internet connection, a point-to-point connection, or other network connection and combinations thereof. The network 103 may be any other type of network that is capable of transmitting or receiving data to/from host computers, personal devices, telephones, video/image capturing devices, video/image servers, or any other electronic devices. Further, the network 103 is capable of transmitting/sending data between the mentioned devices. Additionally, the network 103 may be a local, regional, or global communication network, for example, an enterprise telecommunication network, the Internet, a global mobile communication network, or any combination of similar networks. The network 103 may be a combination of an enterprise network (or the Internet) and a cellular network, in which case, suitable systems and methods are employed to seamlessly communicate between the two networks. In such cases, a mobile switching gateway may be utilized to communicate with a computer network gateway to pass data between the two networks. The network 103 may include any software, hardware, or computer applications that can provide a medium to exchange signals or data in any of the formats known in the art, related art, or developed later.

In a preferred embodiment, the line-of-sight interactive digital badge device (badge device) 101a, 101b is worn on one or more body parts of the user, such as chest, wrist, waist, neck, arm, leg, abdomen, thigh, head, etc. Further, the badge device 101a, 101b may be a wristband, a watch, an armband, a necklace, a headband, an earring, a waist belt and, or a ring. Alternatively, the badge device may be any reconfigurable display that may be temporarily or permanently affixed onto a garment of a user. In yet other alternative embodiments, the reconfigurable display may be a flexible OLED tube or screen interwoven into the fabric of the garment. Badge devices 101a, 101b may have a device visual display that is situated in any one of a person's line of sight. The device visual display may be a single center display, wherein the symbol and, or color-coded visual display cueing a permission to approach and further interact is displayed on the single, center visual display. The same single, center visual display may also display the NVP content. The same display may also be enabled for touch-screen interactivity. In other embodiments, interaction with the display contents may be controlled by controls disposed on a side, top, or bottom wall of a (circular or square) device casing. In yet other embodiments, the device visual display may be comprised of a dual display: a center device display and a surround device display. Each display sharing display functions or having unique display functions. For instance, in some embodiments, the surround device display may display the symbol and, or color-coded visual cues encoding for a permission to approach and interact, while the center device display may strictly display the actual NVP content (a static or a rolling line of user-content images).

In some embodiments of the badge device 101a, 101b, sensors may be disposed within the (domed) device housing, or on the (circular or square) device casing, to capture at least one of a user environmental or contextual data to further inform a user mood, emotion, physical condition, mental well-being, and, or willingness to be approached by other digital badge users for further interaction. The digital badge device 101a, 101b is first sent to the mobile communication device 102 and thereby, sent to the processing unit over the network 103. The digital badge device 101a, 101b communicates with the mobile communication device 102 over a short-range wireless communication medium, such as Bluetooth, etc. In other embodiments, sensor input may be derived from devices other than the badge device 101a, 101b. Device input may also encompass the sensor-captured raw data input or transduced and processed data input from any other device associated with the user, such as devices worn, mobile devices, and, or fixed-access devices, such as Internet-of-Things devices (e.g., smart thermostat, home automation consoles, etc.). The plurality of device inputs provides additional input for aggregation and behavior profiling, thus layering the behavior profile with additional context for generating a higher fidelity of user mood, emotion, well-being, etc. This higher resolution of user profiling may update the user interaction rules and, or policy for determining access for approach and activating further digital event/content interaction.

In continuing reference to FIG. 1 and the exemplary environment of the NVP system, a mobile communication device 102, such as a smart phone, is a portable device that has the capability of communicating over the network 103, presenting dashboard provisioning based on a respective digital badge device 101a, 101b pairing. Examples of the mobile communication device 102 include, but are not limited to, a smartphone, a tablet, a personal digital assistant (PDA) and a mobile phone. The mobile communication device 102 may be paired with a respective digital badge device 101a, 101b over a short range wireless communication medium. Examples of the short-range wireless communication medium include Bluetooth, ZigBee, Infrared, Near Field Communication (NFC) and, or Radio-frequency identification (RFID). Likewise, the digital badge device 101a, 101b may interact with other digital badge devices 101a, 101b using a short-range communication protocol, such as Infrared, Bluetooth, ZigBee, NFC, and, or RFID.

Preferred embodiments may include the addition of a remote server 105 or cloud server to further provide for back-end functionality and support. The server 105 may be situated adjacent or remotely from the system 100 and connected to each system 100 via a communication network 103. In one embodiment, the server 105 may be used to support user behavior profiling; user history function; predictive learning/analytics; alert function; network sharing function; digital footprint tracking; e-commerce/advertising platform support, etc. The remote server 105 may be further configured to authenticate the user and retrieve data of the user, device, and, or network and applies the data against a library of validated user information for enabling a payment or ticket transaction at a fixed-access point deploying an embodiment of the interactive badge device 101a, 101b.

Figure 2:
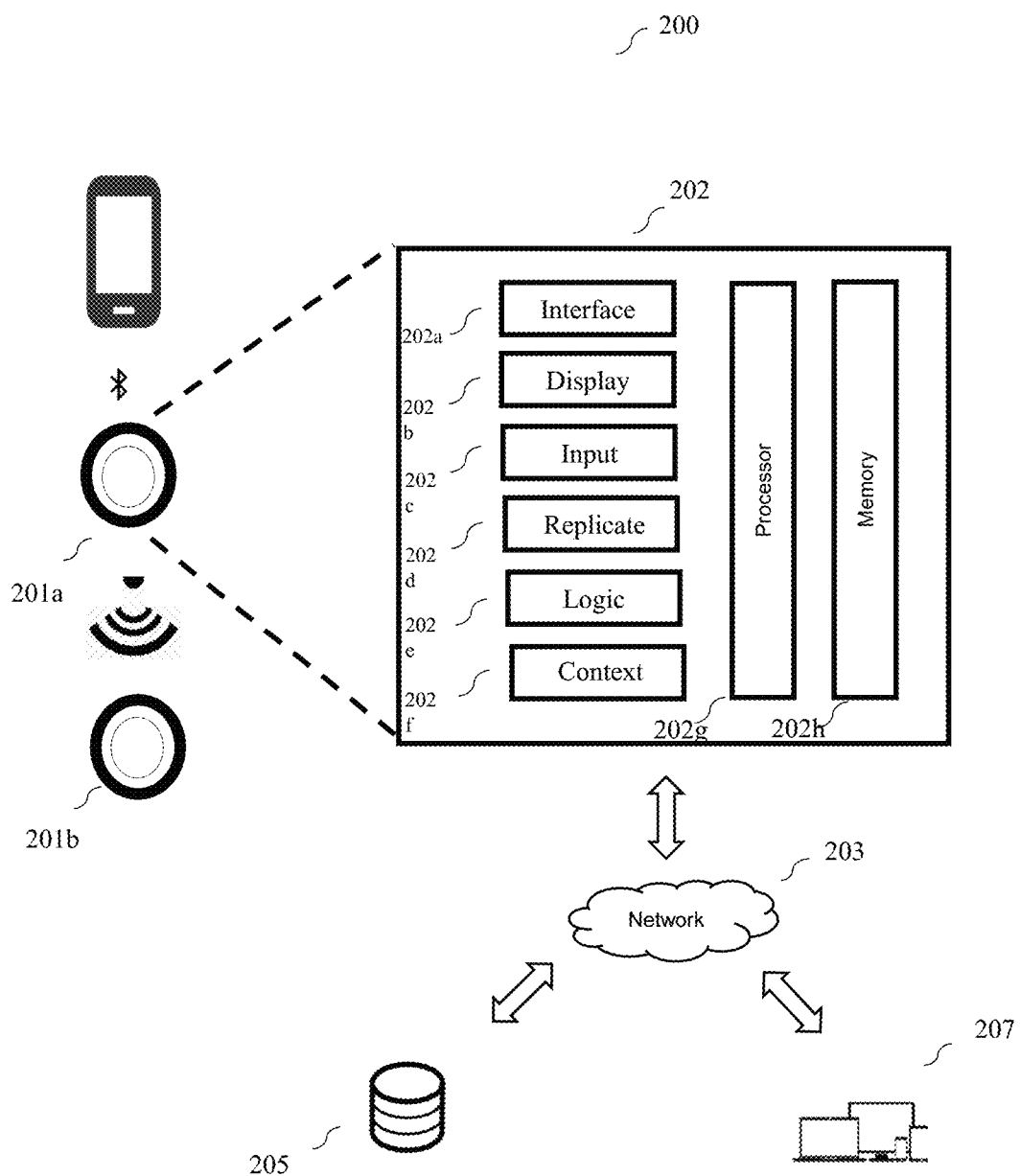
FIG. 2 illustrates a block diagram of the NVP communication system in accordance with an aspect of the invention.
Figure 3:
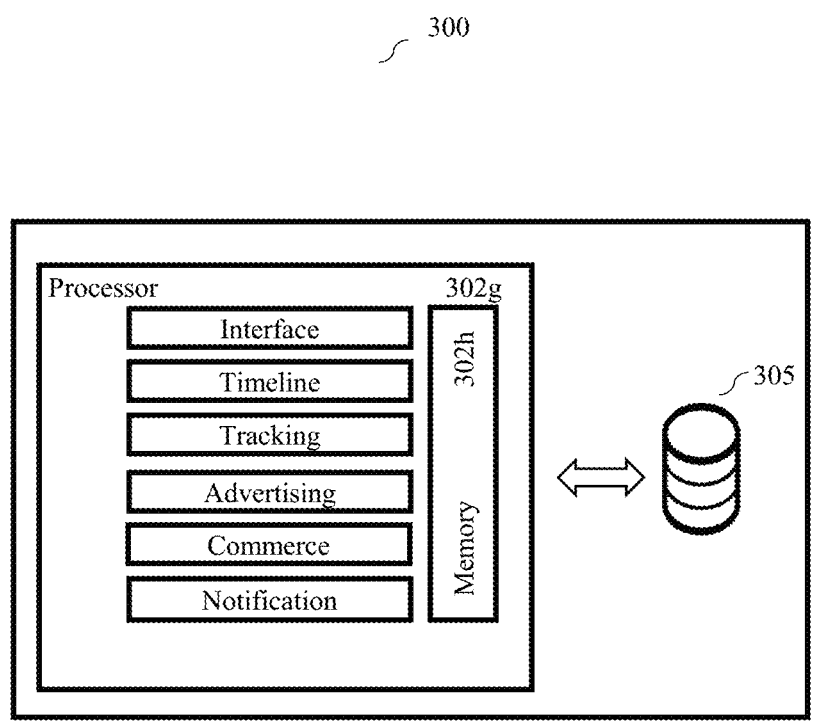
FIG. 3 illustrates a block diagram of the NVP communication system in accordance with an aspect of the invention.

Now in reference to FIGS. 2 and 3. FIGS. 2 and 3 both illustrate an exemplary embodiment of the NVP system. FIGS. 2 and 3 illustrate an exemplary processing unit 202g, 302g used for displaying a visual cue for permission to approach and, or a content display for exchange between interactive badge devices 201a, 201b or sharing over a network 203. As shown, the processing unit 202g, 302g may be communicatively coupled to at least one of an interface module 202a, display module 202b, input module 202c, replicate module 202d, a logic module 202e, a context module 202f, an interface module, a timeline module, a tracking module, an advertising module, a notification module, and a commerce module. The processor 202g, 302g may also communicatively coupled to a remote database 205, 305 and a memory 202h, 302h. In an embodiment of the present invention, the processor 202g, 302g includes a notification/alerting module. The notification/alerting module is configured to generate reports at regular intervals (such as daily at 12:00 PM, weekly and monthly), on-demand (when the user requests for a report corresponding to the user), or when triggered by a digital event. Typically, a digital event may be defined as any digital display for badge-badge display or network sharing or server authentication. The notification/alerting module may double up as a tracking module, wherein a user may keep track of his or her physical displays and interactions, as well as his or her virtual displays and interactions. In an embodiment of the present invention, the notification/alerting module may also be configured to send a notification to the user of the growing social influence of a user. In other words, an influence metric may be pushed quantifying how may people I have interacted with, and how many times my virtual NVP line of content been shared with other users on social media. The notification may be a message, a phone call or any other communication means.

In an embodiment of the present invention, the processor 202g, 302g includes a timeline module. The NVP line of content may be displayed or pushed in at least one of a static, dynamic, and, or scheduled fashion on at least one of the user's center device display based on at least one of the user's scheduler criteria. The line of static, dynamic, and, or scheduled images and, or video NVP content from at least one of the user's to be displayed on at least one of the user's center device display may be curated by the user, pre-set, or dynamically pushed based on any one of user parameter. In some embodiments, the timeline module enables the displayed line of static, dynamic, and, or scheduled images and, or video NVP content to be further replicated on at least one of a digital and, or virtual presence of at least one the users. In other words, the timeline module enables the displayed line of NVP content to be further shared with social media and digital media outlets, over a network. In some embodiments, an Application Programming Interface may be integrated and configured for enabling transfer and, or further interaction of the replicated line of static, dynamic, and, or scheduled images and, or video NVP content.

The processor 202g, 302g may include an advertising module and, or a commerce module, enabling advertisers to target users for NVP content display based on NVP activity or influence of said users. The advertising module may further comprise a bidding module, wherein the advertisers bid among each other for engaging a user for incorporating a winning bid advertisement into the NVP content display of the user. The processor 202g, 302g may further comprise a commerce module, wherein users may purchase digital downloads of NVP content for NVP content display. The commerce module may further be coupled to a distributive digital ledger, wherein each NVP exchange among any user is represented as a unique node in the digital ledger. Each node tagged with meta data facilitating at least one of a transaction, validation and, or registration for each NVP exchange.

In some embodiments, any one of the processor functioning mentioned above may be off-loaded to the processor of the mobile device and, or the remote server. The device display may simply be used for display function for both symbol and color-coded display cues on any one of the surround display and, or center display, and NVP line of content on the center display.

Exemplary Communication Protocol

The NVP language is made up of symbols, shapes, colors and images that when combined form a language specifically for the person to person or groups of people interactive badge or screen market. This language is the only language that allows individuals to communicate with the interactive badge in a visual sense. The NVP may be displayed on a surrounding of the interactive badge device and, or on device center display. In some embodiments, the surround display and center display may be combined in unison, or in a sequential manner, to express the NVP language.

The NVP Language Components

Figure 4:
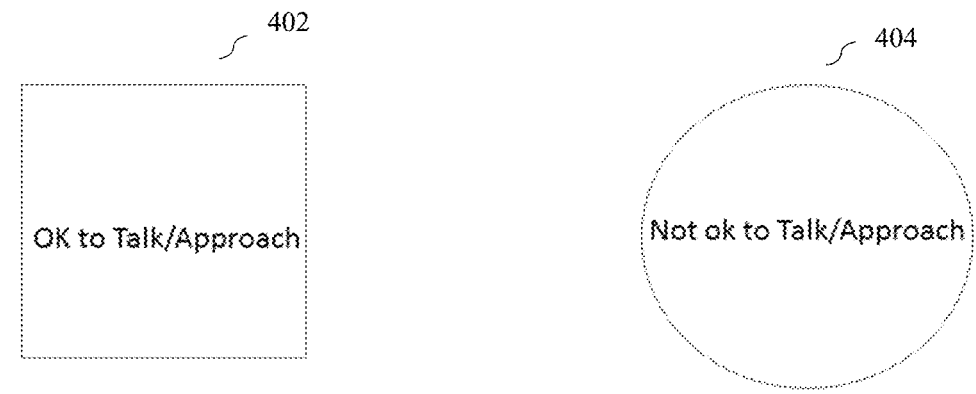
FIG. 4 illustrates a symbol and, or color-coded NVP communication protocol in accordance with an aspect of the invention.

The first component of the language is a shape such as but not limited to a square, circle, triangle or star. These shapes indicate to the viewer a behavioral welcoming state of the person viewing them. One such behavioral state might be a welcome to communicate or not as the case might be. An example of these shapes and their uses are shown in FIG. 4. This first component forms the frame of all the communication symbols to follow. It is programmed by the NVP wearer at the start of a badges or screen or display wearing session.

Figure 5:
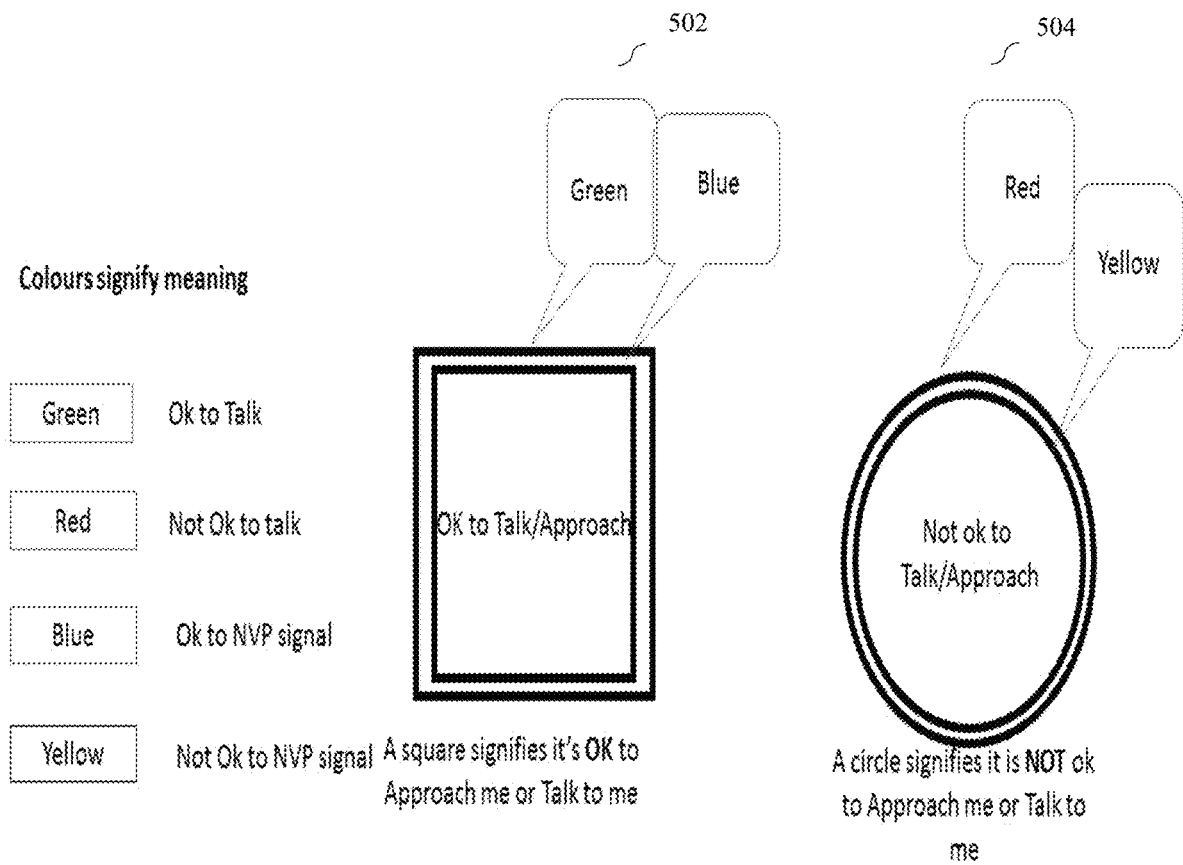
FIG. 5 illustrates a symbol and, or color-coded NVP communication protocol in accordance with an aspect of the invention.

The second component of the NVP is the color of the first component. This color signifies the rules of communication and engagement with the wearer and the receiver. The color signifies whether a person is willing to accept a communication and what type of communication from the viewer. The color can be part of the symbol or a color displayed on or around the badge. An example of this is shown in FIG. 5.

Figure 6:
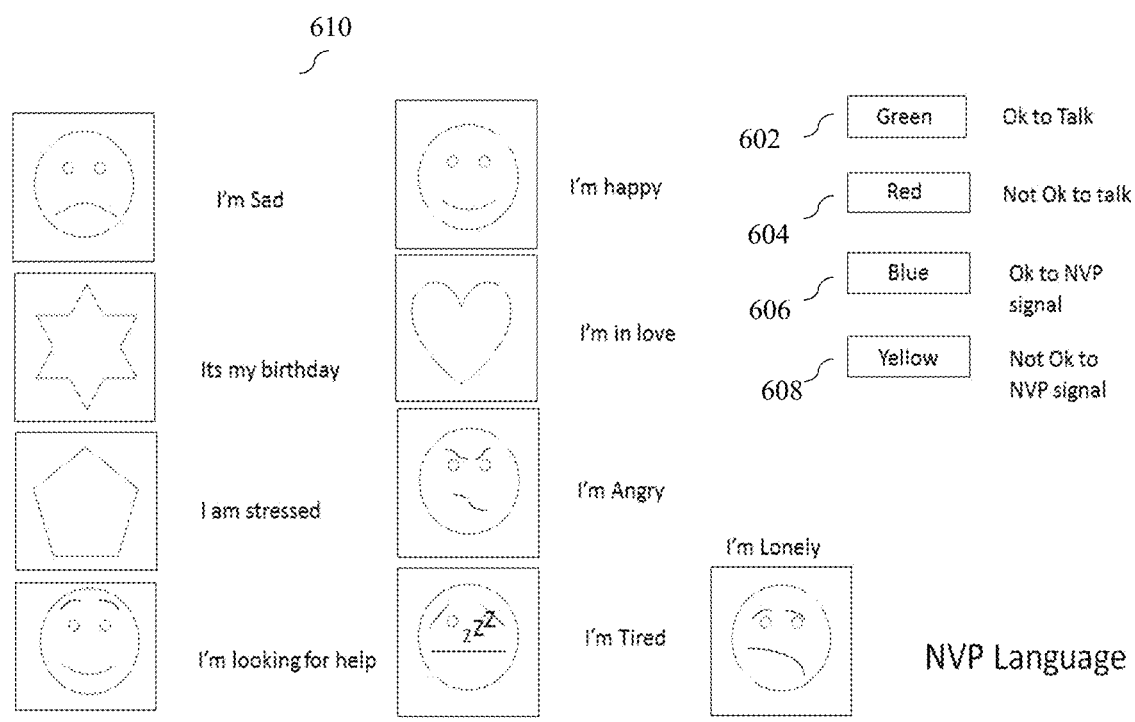
FIG. 6 illustrates a symbol and, or color-coded NVP communication protocol in accordance with an aspect of the invention.

The third component of the NVP is the symbol within the colored shape. These symbols can be anything which conveys a message to the viewer from the wearer but can only be shown using the NVP programming protocol described later. These symbols can be programed to be shown for a certain amount of time using the NVP programming software scheduler and these symbols can also flash based on that scheduler. These symbols can be different colors based on the person's mood. Some examples of the symbols for NVP are shown in FIG. 6.

In a preferred embodiment, disclosed is a non-verbal line of sight electronic communication protocol, the protocol comprising a non-verbal symbol language for communicating wirelessly over electronic devices, including interactive badges and, or displays, between users and, or static receivers, who are in one another's line of sight; and the symbol language displayed on the interactive badge and, or display and, or static receivers communicate whether a first user can approach at least a second user or not for further digital interaction.

For instance, the interactive badge or display that is displaying a blue square 402, 502, 602, which indicates that it's ok to approach me. Inside of which a green square 606 indicates its ok to talk to me and send me a NVP communication and a lonely face 610 from the symbols show that I am lonely. This symbol is programmed to the badge using the NVP programming language software which allows for timing and scheduling. The color of the symbol is the open or closed gateway to the receiver. If the color is not correct the communication will not pass. Alternatively, in other embodiments, any combination of shapes and, or colors may be arbitrarily chosen to signify a permission to approach or activate a further digital content interaction. For instance, a green circle might suggest permission to approach, and a blue square contained therein may suggest a permission to exchange an NVP line of content. Choice of colors, symbols, and the interaction with each, may be purely arbitrary.

The NVP Programming Interface

Figure 7:
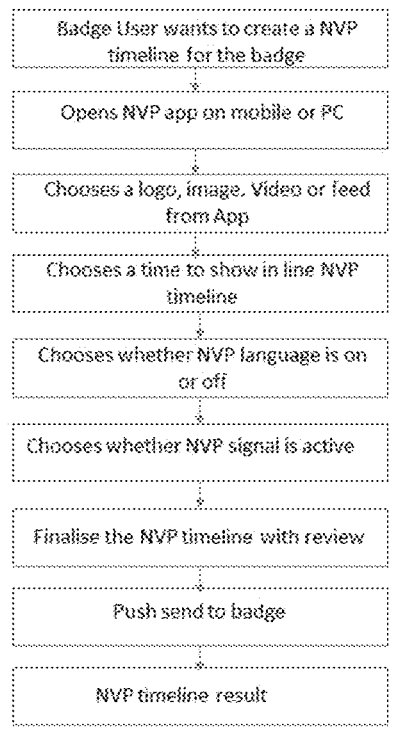
FIG. 7 illustrates an NVP content programming process flow in accordance with an aspect of the invention.
Figure 8:
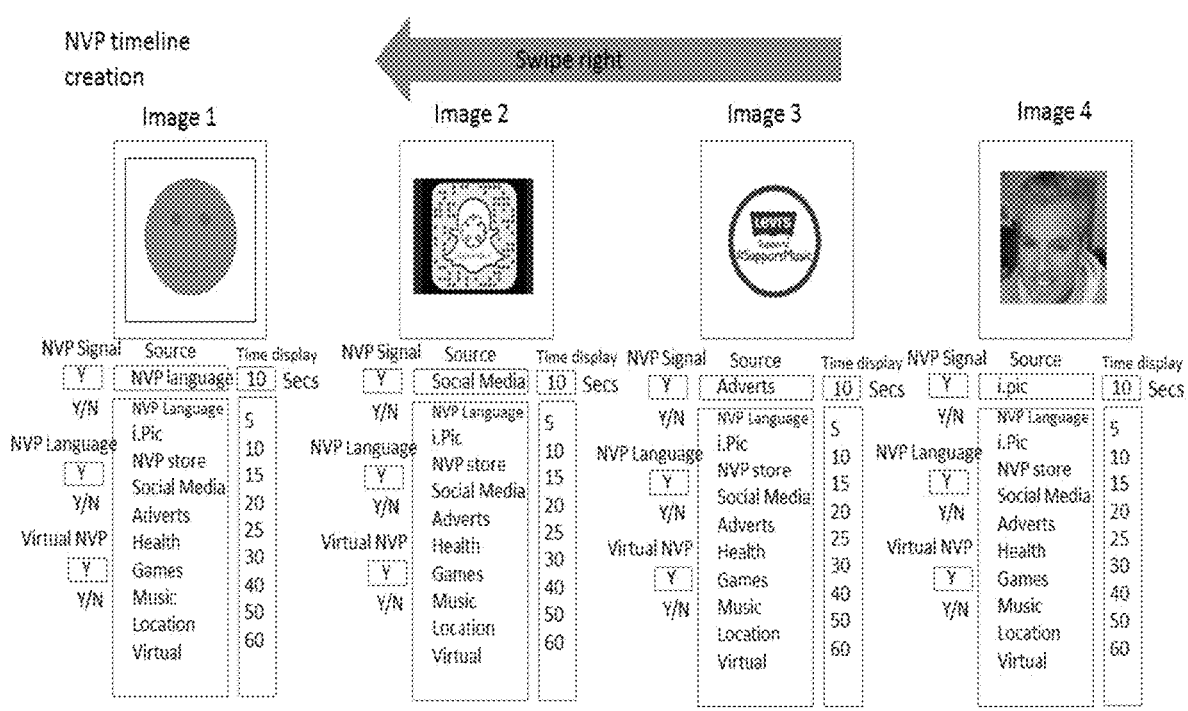
FIG. 8 illustrates a screen shot of a scheduler criteria in accordance with an aspect of the invention.
Figure 9:
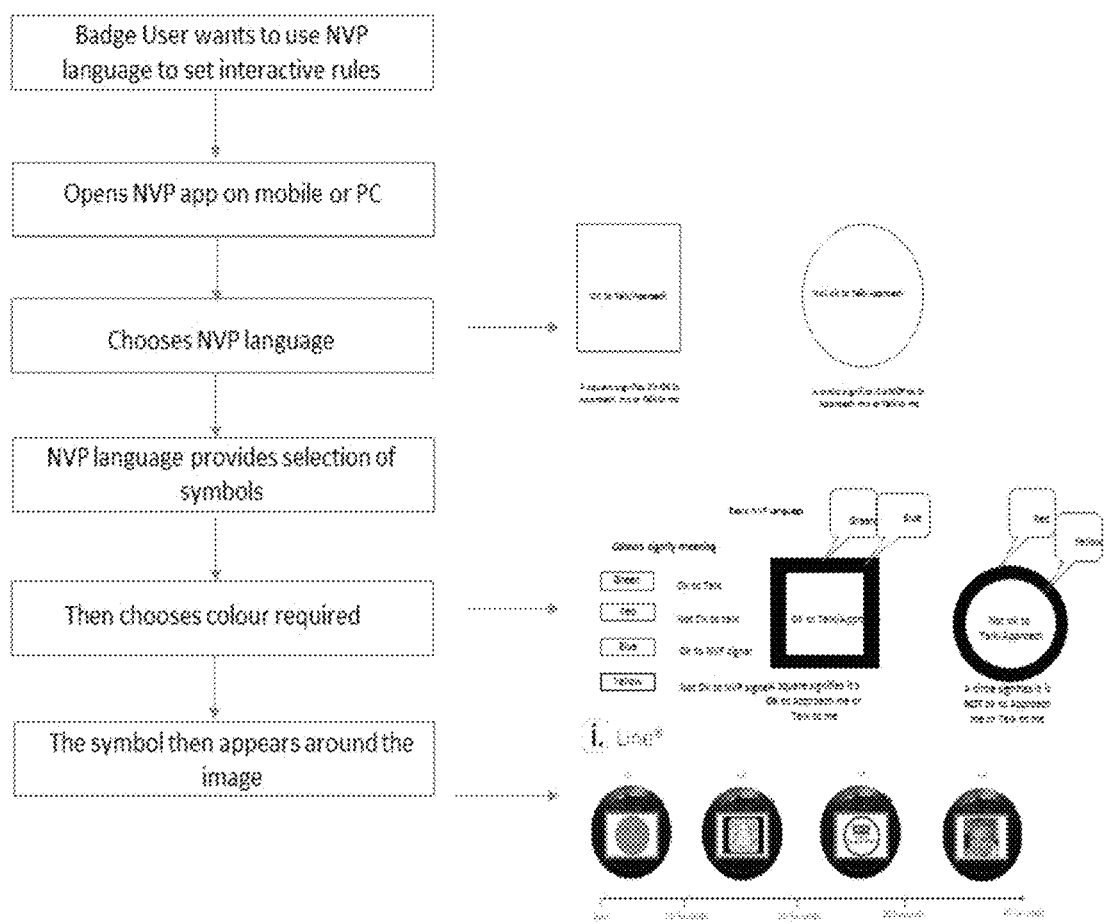
FIG. 9 illustrates an interaction rule process flow in accordance with an aspect of the invention.
Figure 10:
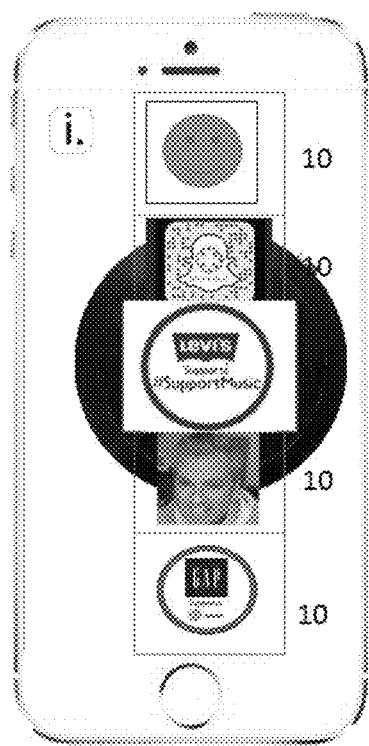
FIG. 10 illustrates a screen-shot of an NVP content display in accordance with an aspect of the invention.

To allow a wearer to program their interactive badge or personal digital display, a programming interface is required which allows the wearer to set up the language on the badge and run it throughout a day as a timeline. This requires a process which is described in detail in FIG. 7. In a preferred embodiment of the process, the wearer decides to program the badge or display with the NVP language; the program which runs on the connected device (smartphone or PC) is opened and the language variables are displayed; the NVP language components 1, 2 and 3 can be selected; the ability to send a communication to another wearer can be selected; and the ability to send the entre NVP wearers timeline can be selected. Additionally, the NVP program allows the wearer to select images from their own images, from the NVP store, feeds from interfaces with social media applications, from adverts selected from the NVP advertising platform, from health devices, from games, music and programming from a specific GPS location. Additionally, the amount of time an image is displayed may be programmed with the resulting timeline transmitted from the device to the wearable badge (FIG. 8). The process for setting the rules of interaction and engagement is further set out in FIG. 9. Once the NVP time line is set, this is transmitted to the badge and can be altered in real time. An example of this in vertical format is shown in FIG. 10. Alternatively, the line of NVP content may be depicted or scrolled in a horizontal fashion.

The NVP Communication Protocol Standard

Figure 11:
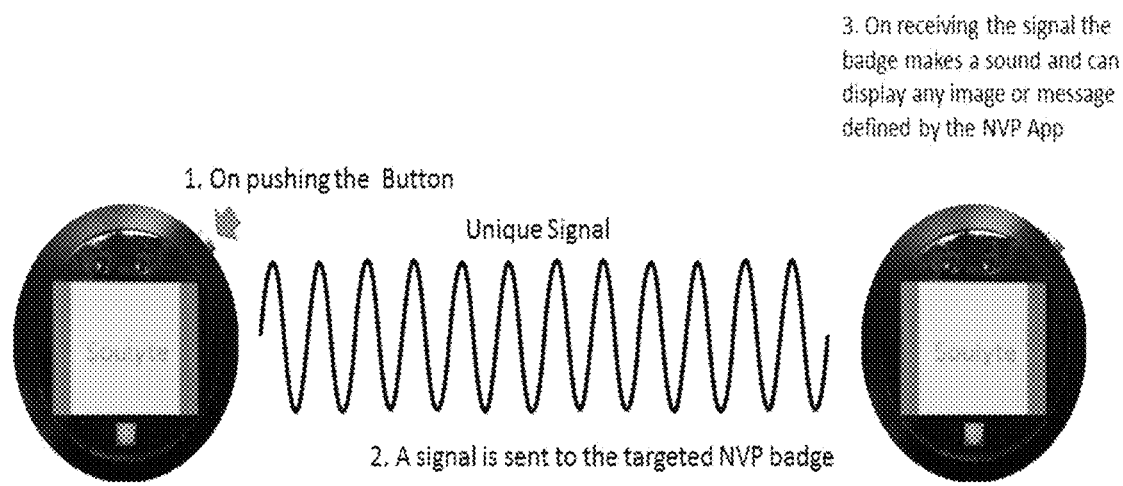
FIG. 11 illustrates a badge-to-badge interaction in accordance with an aspect of the invention.

As illustrated in FIG. 11, the NVP communication system allows one individual who is wearing an interactive badge or screen—in the line of sight of another individual wearing the same—to send messages wirelessly based on the NVP displayed. The message can only be sent if the NVP is set to the correct parameters set out in the NVP language section of this document. The NVP protocol has a unique number attached which allows the receiving interactive badge or screen to decode it and activate an event such as but not limited to an image display, a sound played, a vibration, or a signal sent back to the sender or a signal being sent to the parent smartphone, which in turn activates an event.

This NVP signal is defined as a unique wireless signal sent from one interactive badge or screen to another over a certain physical distance in line of sight. Using the NVP signal, the interactive badge can send an NVP signal to any number of badges or receivers and the badge can accept an NVP signal from any number of badges. The NVP signal can only be accepted if the correct NVP symbols are being displayed. By accepting an NVP signal this can trigger the interactive badge or screen to display anything it's been programmed to by the NVP app running on the smartphone or PC. If accepting the NVP signal this can trigger a sound or vibration or cause a device to trigger a sound or device. On accepting the NVP signal this can trigger the NVP app running on the smartphone to activate an event or process.

On accepting the NVP signal, this can trigger the interactive badge or screen via the NVP app to display a set of offers, images, videos or sounds.

In a preferred embodiment, a non-verbal line of sight electronic communication protocol is disclosed, the protocol comprising: a non-verbal symbol language for communicating wirelessly over electronic devices, including an interactive badge with a line of sight device visual display, between users who are in one another's line of sight; the symbol language further comprising a set of any shaped and, or colored symbols that are programmably displayed on the device visual display, wherein the device visual display is at least one of a surround device display and, or a center device display; and based on the programmably displayed set of shaped and, or colored symbols on the device visual display, communicate whether a first user can approach at least a second user or not for further digital interaction.

The technology used to send and receive the NVP signal can be at a specific frequency with a unique number. This has the effect of making any other device not able to recognize the NVP signal or be able to manage the events that have been set by parameters with in the App. This unique number and encryption method makes the NVP interactive badge or screen only recognizable with another NVP interactive badge or screen or receiver or a licensed piece of 10 hardware and software from the NVP group of products. This will be a critical area of protection for the NVP language and protocol as without it other manufacturers will not be able to enter the market as people will not be able to interact with their badge. The NVP language is the standard for interactive badges and devices. In short, the NVP signal can be a visual equivalent of a click through.

The Virtual NVP Line

Figure 12:
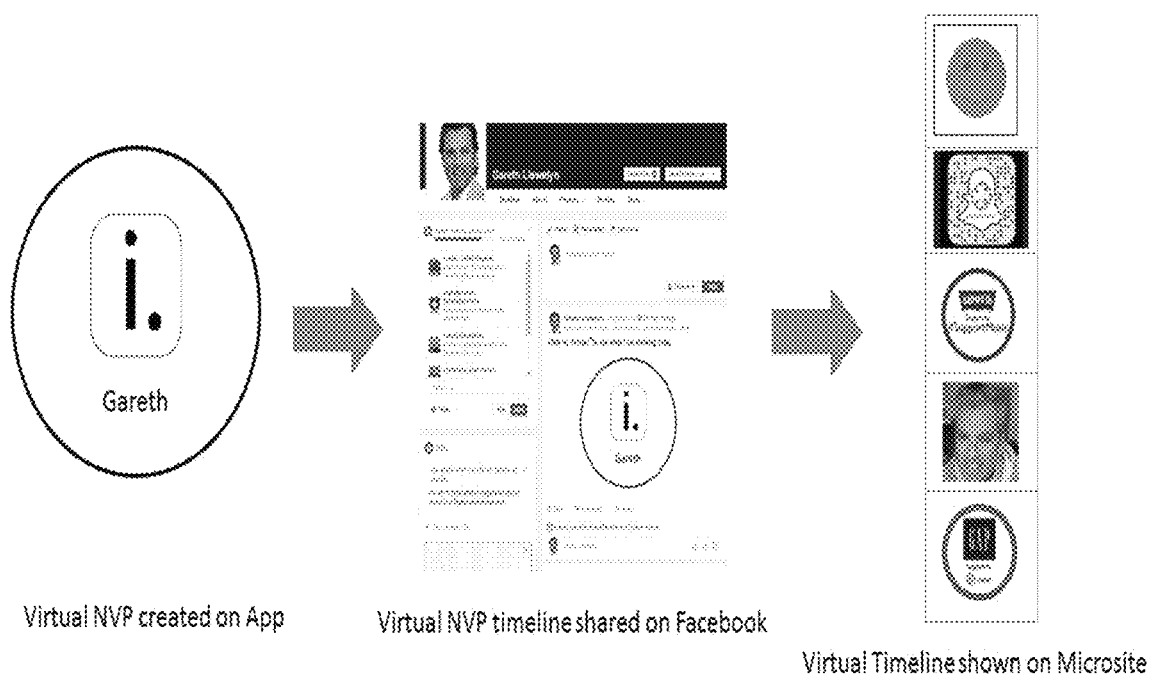
FIG. 12 illustrates an NVP content flow in accordance with an aspect of the invention.
Figure 13:
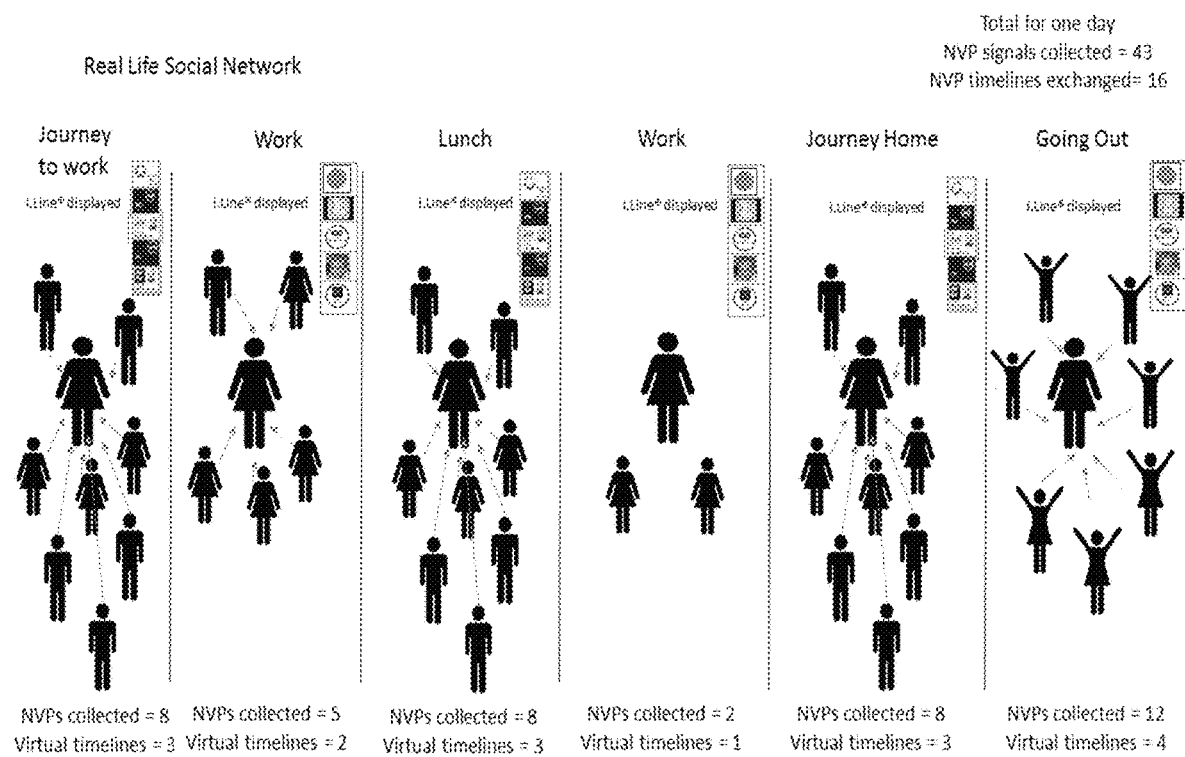
FIG. 13 illustrates a screen-shot of a virtual NVP timeline in accordance with an aspect of the invention.

FIG. 12 illustrates the transition from badge 1 display; share with badge 2; and digital media share of badge 1 display with tracked footprint (badge 2 share). Virtual NVP is the digital version of the visual NVP line shown on the interactive badge or screen that can be made available to NVP badge users so they can see what others are displaying on their NVP badges that day. There are two uses for the Virtual NVP line: 1) to allow NVP badge wearers to transmit their NVP line from one user to another; and 2) to allow NVP badge wearer to attached their own.

The pre-defined presentation of the content message on at least the interactive device visual display and, or virtual profile may be configured for network or digital sharing.

Furthermore, the virtual profile may, via an Application Programming Interface, be configured for transfer and, or further interaction such as geo-location, site check-in, etc. In other embodiments, the NVP system has been developed so there is a very low entry point for integration to the program. In fact, as the user is only taking a screen shot of their phone for any media there is no integration with 3rd parties necessary. By way of an example, a user could construct a NVP line of their Facebook post, Twitter post, dashboard from Fitbit, images from their phone and a mood image. All of these can be taken directly from screenshots with no outside integration from developers needed. These screen shots can be real time based on the time of NVP line creation. In some embodiments, live data feeds from monitoring devices would be image related, so rather than display on the device, a mirroring program would allow the device display to be shown on the NVP badge via Bluetooth. This NVP 'Llego' block is a universal interface to all monitoring and real time feed devices.

As each person is responsible for their own NVP line they are responsible for the content that is published. However, the NVP system has a safe guard to ensure that inappropriate and copyright content is not displayed. Each time an NVP line is created it must pass through the NVP 'Llego' Block server to pick up any illegal images. If this happens, the NVP line will be rejected and the user asked to review the images. The NVP 'Llego' block interface allows media channels to display their content on the NVP badge if the user so wishes. These channels are passed through the NVP Llego block centrally and are available for users to connect to if they so wish using the NVP line creation software. There are many markets for the NVP interactive language and its communication protocol. The application that follow are just some examples Application 1:
Advertising Targeting The groups are based not on where you are digitally i.e. Facebook or Twitter but where you are physically i.e. on a train, at a concert, at a bar or at work. We will be able to count how many NVP signals were sent to individuals and what they reacted to. In this way new physical influencers will emerge, i.e. those who are the most popular. These peoples virtual NVP lines will be the most desirable from an advertising perspective as they will enhance their online profile with that running on their interactive badges or screens. The diagram shows what might typically happen to a person wearing and actively using the NVP language on a daily basis.

As illustrated, girl A has collected 43 NVP signals and had 16 conversations about the NVP line she is displaying. If she has configured her NVP line correctly each person who has sent an NVP signal will have received her Virtual NVP Line. which was reacted to. Note that girl A had configured two NVP lines for different parts of her day. So different people will see different NVP line. What is clear is that as the NVP language and communication protocol becomes established the number of transactions will grow exponentially as each of the above people will have their own NVP badge and their own NVP line We will quickly see the emergence of the top real life influencer in a daily basis. Advertisers will be able to target the most popular real time influencers based on NVP sharing activity.

In other embodiments, the advertising module or platform may further comprise a bidding module, wherein the advertisers bid among each other for engaging a user for incorporating a winning bid advertisement into the content message display of the user. Advertisers will be able to use the NVP Real Time Bidding Network to get access to the NVP line of targeted individuals if they have given their consent to take advertising in their NVP Line. These adverts will be clickable on the Virtual NVP line so they can be transferred from one user to many in the Real Life Network®. This potentially gives advertisers a major new network of people to target based on their location.

Application 2:
The NVP Store or Shop Controlling the NVP Content

Images will be able to be taken from a person's phone and shown on the NVP badge. As these are put onto the NVP line through the NVP App, we have control over the content and can manage any indecent, or inflammatory content. However, the final say will be with the NVP badge wearer. We will have complete control over the Virtual NVP line and be able to stop the distribution of any indecent or inflammatory content. Additionally, there will be a place to purchase widgets that link directly to apps such as Facebook, Twitter and other apps that have integrated with our NVP Llego Block. Brands, Apps and advertiser will have to pay to be allowed on the portal and be subject to our terms and conditions. We expect this fee to be a % of any purchase price or a fixed fee based on an individual's use. i.e. if the wearer wants to buy a specific logo or album cover, they can buy this for a one-off fee from the supplier. We would retain 10% of the retail revenue. This logo would be allowed to be used on the individuals NVP badge, but not be transferrable to another person NVP Line via the virtual NVP line which is read only.

The payment transaction system may incorporate block chain technology, wherein each NVP exchange or digital content purchase transaction among any user is represented as a unique node in the digital ledger, each node tagged with meta data facilitating at least one of a transaction, validation and, or registration for each NVP exchange or digital content purchase transaction. Alternate payment systems may be used, including linking directly to a credit card, debit card, and, or bank account. In yet other embodiments, payment systems may include an intermediary or 3rd party system providing payment processing between users or between user and the NVP store. An intermediary account or escrow-type account may also be used, whereby funds are disbursed from a user 1 account to a user 2 account, or from a user 1-linked intermediary account to a user 2 account upon full satisfaction of transaction or bidding obligations. The intermediary account may be viewed as a pre-paid account. In other embodiments, digital sellers may target users who have pre-paid an intermediary account for a specific item, thereby competing over a particular purchaser for a specific items.

Moreover, in some embodiments, the NVP communication protocol standard may be incorporated into the payment transaction system coupled to the commerce platform or NVP store. For instance, a yellow square on the surround display or center display of the interactive badge may signify that the user is willing to purchase a digital content for download or a physical item. In other embodiments, the yellow square displayed may signify that after scanning a physical item tag, the user's account or intermediary account has a sufficient balance to afford the item. Contrastingly, a red square may indicate that the item may not be purchased based on available balance. In yet other embodiments, a green circle may signify that a payment transaction is confirmed.

To run through a potential scenario, two individuals have bought an interactive badge which runs the NVP language, communication protocol and programming language. Each one has programmed their badges to run a 6-image timeline changing every 30 seconds. They both get on a train in the morning and find themselves sitting opposite one another. Individual 1 sees that individual 2 has a green square framing their timeline of images and knows that this signifies that the person is open to a conversation, is open to receiving an NVP signal and is open to receiving a virtual NVP timeline from this person. Individual 1 decides to send a NVP signal which causes the individual 2's badge to display a 'Hi', beep a sounds and flash once as this is standard for the NVP badge.

Individual 1 approaches Individual 2 and starts to discuss their images. Individual 1 also decides to send their virtual NVP timeline to individual 2. At the end of the day Individual 1 and 2 are able to read how many people have sent them a message, from whom and about what. This scenario can happen at any time of the day and the individuals can change the NVP components in real time through their App. Furthermore, individual 1 or 2 can purchase specific digital content from a coupled commerce platform to be displayed on their NVP line or virtual NVP. What's more, advertisers may target either individual 1 and, or 2 for advertising display based on individual 1 and, or 2's tracked activity.

Moral and Legal Implications:

What happens if a person approaches another person in direct contradiction to the symbol being displayed? There needs to be method of creating sanctions or no-go areas. One component of the moral code is to set a rule saying that if a person is reported more than 3 times for infringing the person space their badge and account will be suspended. But what happens if the person does not have a badge and approaches the person with the approach symbol anyway. What can be done in this circumstance? This is where a moral code needs to be created or at least set out. An unwritten rule which adheres to normal law is that a person has the right to tell the person that they do not want to talk even though they have that symbol displayed.

Additionally, how much personal information can be displayed on the interactive badge without it causing someone offence and who is monitoring, censoring and controlling this content? Through the app, we are able to control what is displayed on the device, but this requires monitoring at the server side and will require human intervention. Again, this is where the moral code component of the ecosystem comes into play. The alternative is to let the general public publish what they like on their own badges or displays. If this is offensive, is it covered under the relevant laws of the country? How much control should we exercise over the content displayed in public? Every badge sold should have an ethics card included which states our ethic culture and what can and cannot be displayed. If anyone is shown to be contravening, it would be seen as contravening badge sub-culture or badge mores.

Interactive mobile, wearable or portable badge system includes one or more electronic device, pair-able wirelessly with other electronic device(s) wherein at least one device programmably changes media state such as color or other attribute, such as according to user donation to charitable application, or other service or condition. Wireless interaction may be configured exclusively between devices.

At least one device may display image/video, or change color programmably according to social media interaction. Automated system displays individualized color donation, for example, by determining individual level of donation to charity or cause, preferably to display colors electronically showing determined level of donation.

Personal attribute may be displayed automatically by designing unique color sequence corresponding to personal advocacy index, mood, medical condition, age, availability, physical movement, and/or music frequency.

Magnetic attachment element(s) may include magnetic/magnetizable material to facilitate clip-able assembly, such elements configurable as interactive personal badge for displaying programmable color sequence; element may comprise flying saucer design having magnetic clip with domed glass screen.

Further in accordance with one or more aspect of present novel approach, one or more commercial, marketing, or advertising brands serve to promote business value, including various cause such as philanthropic, charitable giving to general public, for example; and such cause is relatively difficult to achieve though conventional product marking or labeling.

Since brands desire to prolong interaction with branded product/service, it is contemplated generally herein to provide novel interactive badge device and/or method that endeavor advantageously to enhance longevity to promote brand value to general public, as well as provide method for displaying such value from/to various badge wearers.

For instance, contemplated interactive badge may demonstrate value visibly via uniquely associated color sequence, e.g., donation amount, charitable cause, preferably via smartphone-badge interaction.

In particular, it is contemplated that interactive wearable badge is functionally configured or programmed with software, for example, which when connected to web app on smartphone or computer and wireless connection, such as Bluetooth, displays data, image or video and barcode generated from content management system. Thus, displayed barcode read via smartphone app causes data to be collected and/or processed, interactively such that message, advertisement, internet site link, or other information is transmitted to smartphone or other portable multifunctional electronic device.

Advantageously, real-time messaging is displayed by interactive badge to badge owner/user of badge controller exclusively per configured web app and/or associated content management system. Also badge color may change according to owner social media usage and/or content management system. Optionally, smartphone transmit message according to user location.

Thus, interactive badge may link wirelessly via Bluetooth, for example, to smartphone that transmits message based on user preference, such as music, rewards, charity donation, etc.

Donation amount transmitted to charity may automatically change badge color, and/or display brand logo, image, video, or barcode. Thus, badge color may display automatically red for lowest level to orange to yellow to green to light blue to dark blue to white, representing highest level of donation amount.

Also, badge color may display automatically according to emotional criteria or "heavenly score" associated with personal mood. Optionally, interactive badge configured with software programmably to transmit individual barcode containing link to website or social media account or to web app, preferably configured according to badge application programming interface using one or more controller and/or software application, as well as optionally communicating according to Near Field Communication data format or wireless protocol.

For example, such controller automatically sends color sequences, images, barcodes, as well as temperature, GPS location, or social media for display via badge screen interface. Also such controller automatically enables interactive badge charging via wireless charging point. Furthermore, magnetic ring element may facilitate badge attachment.

In one embodiment of the present approach using such controller, one or more computer program or mobile/web application automates social advocacy platform allowing users to share media content tagged with donation from one or more brand, for example, so when viewed, brand donates small sum to cause. Accordingly user dashboard shows charitable amount donated automatically per brand. Wireless system may integrate electronic badge interactively using controller application visually, for example, so charity supporter electronically displays support for cause via badge display.

Thus, during programmed operation, badge may display amount currently raised via pattern and/or sequence of colors, including charitable logo, sponsoring brand, and/or barcode scan-able to id other associated or commonly interested users, i.e., "soul-mate" via smartphone or other wireless network connectivity. Hence, badge user self-identifies, for example, to share personal cause, state of mind, mood, caring nature, philosophy of life, etc., electronically, digitally, physically, proximately, spiritually, emotionally, etc.

In another embodiment, user subscribes automatically via wireless app to advocate charitable cause, while also sharing such advocacy via social networking, e.g., Facebook, Twitter, etc., such that one or more sponsoring brand donates to such cause. Then, such subscribing user may be alerted by the app that such social networking advocacy is automatically display-able on user interactive badge. Preferably, such user subscribes to wireless app, since subscription may be apportioned to charitable cause. Optionally, user badge and smartphone devices running such app may be cooperatively paired to synchronize or otherwise facilitate interactive display on badge and/or smartphone various multimedia and/or graphical elements, such as color circle based on amount raised, sponsoring brand logo, cause logo, user unique barcode link-able to wireless app (i.e., cause and/or sponsor links).

Moreover, in yet another multi-user embodiment, first user interacts with another user via common wireless app by sharing, scanning, or otherwise communicating wirelessly to alert multi-user interaction. Initially, first user automatically indicates or otherwise offers via wireless badge and/or smartphone image, sound, video, or other message indicating interesting interaction or other relevant parameters, such as cause, sponsor, charitable campaign, as well as amount sponsor prepared to donate per click on content. Accordingly, first user clicks on this offering page to access content for viewing and posting on personal timeline. Then, both users dashboard is updated and transmitted, for example, as flash circle signal to wireless app on corresponding smartphone and/or badge. Optionally, when dashboard changes up a level on both users such circle color may change appropriately.

As contemplated herein in accordance with one or more aspect of present invention, terms "Soulyte," "Soulmate," and "LiikeMinded" refer generally to various hardware product device and/or software process technique embodying one or more interactive wearable badge automated programmably as described herein. In particular, such Soulyte may refer as well to various functional attributes, including: badge product look and design, e.g., flying saucer with magnetic clip; badge product functions, e.g., display of jpgs, video, colors based on level of giving and/or mood; badge controller interface and design, e.g., app to control screen from smartphone; software for data transmission from users phone thereto; software for viewers phone to interact with badge via barcode or Near Field Connection (NFC), e.g., when tapped with phone, badge glows light for period; Application Programming Interface for allowing any other entity to connect, e.g., app, PC, device, cloud, etc.).

Furthermore, as contemplated herein in accordance with one or more aspect of present invention, term "MoodWire" refer generally to automated sentiment analysis, embodied in various hardware product device and/or software process technique embodying one or more interactive wearable badge automated programmably as described herein. In particular, such MoodWire may refer as well to various functional attributes for sentiment analysis, for example, including automated hardware and/or software to express personal state of being from spiritual perspective rather than that of personality. Thus, MoodWire may take cues automatically from various aspects that make people feel better about life and themselves. For example, MoodWire may automate making statements of gratitude and truth in morning, and evening a person thereby changes mood and perspective on life. Hence, MoodWire allows person to speak statements of truth and gratitude into such app, and this automated sentiment analysis app thereby may translate such words automatically into various corresponding light on Soulyte badge device.

Also, MoodWire hardware and/or software may operate to listen automatically for parameters, such as tone, volume, and/or specific words, among other aspects, to provide score that may translate into various colors on badge, for example, ranging from red, orange, yellow, green, light blue, dark blue, purple, black, white in a circle of light displayed simultaneously and/or sequentially. Thus, such colors may change automatically based on personal interaction ranging from red as sad, to white being happy and contented.

For example, when Soulyte hardware and/or software determines touching by another person also running Soulyte software, this determination may also affect color of badge of the other person. Via NFC Accordingly in this coordinated manner between badges, such interacting persons automatically become configured as SoulMates via physical albeit electronic connection. Displayed color pattern may reflect personal chakras based on MoodWire software, such badge circle of light effectively shows colors balanced in unison, i.e., well balance and happy person.

Generally, in accordance with one or aspect of the novel system, system and/or approach, it is contemplated herein to automate one or more electronic device, system, hardware, product or programmed technique, process, method and/or other equivalent functionality individually and/or integrated in one or more distributed network, preferably that uses color to rank personal mood, behavior, or state of being.

For example, such novel approach as described variously herein may arise via automated software and/or hardware that effectively rank chakras; also such novel approach may use color in a circle automatically to show how much giving has taken place. Additionally, such novel approach may use color tone, brightness, flashing, and/or sound automatically to indicate wellbeing. Moreover, such novel approach may use speech automatically to indicate state of mind as well as wellness.

Alternatively, such novel approach may use one or more Soulyte-enabled badge hardware and/or software for merchandising to display, for example, band logo at concert event, e.g., sold going in and instructions relayed on screens before concert. Optionally, badge color of ring around light changes based on concert controller system; such badge lighting control may occur through web link or app, i.e., directly to badge wirelessly without download to smartphone. At different points in concert, such color may change in unison.

Also, it is contemplated programmably that when people physically touch other people's badge, such badge may glow lighter, and data is collected from such interaction, optionally via free track or link available when phone taps another person's phone. Also, it is further contemplated programmably that one or more wireless electronic device may use circle of light to be synced with music on badge.

In response to detecting music change, device display color may change accordingly, for example, from red to white sequence, or circle of light may flash in unison with music. Optionally, single source may change color on badge using sound, and badge screen may show logo with barcode and/or cause. Also, it is contemplated that when badge is bumped with NFC interactively, track may be downloaded, or link provided accordingly.

In sports application, such as football/soccer or other competitive and/or entertainment event, one or more badge or other electronic merchandise may be configured wirelessly to light up, optionally with certain team colors, during stage concert or stadium goal/touchdown event proximately and/or remotely, for example, as controlled centrally with associated team or performer via network controller. Optionally, single controller shows light on circle and/or flashes such light; also it is contemplated herein that such light may be displayed by badge in any viewable spectrum; also, crowd noise may cause badge light to come on, or change color or flash.

In healthcare application, one or more Soulyte-enabled badge is provided to patient to monitor condition biometrically, e.g., by pairing Soulyte-enabled badge/smartphone with various devices configured with Soulyte API, such as temperature and heart monitors, cardiac and blood pressure and sugar monitors, and respiratory monitors. Optionally, colors on badge or device ring or screen can change based on patient condition and can alert via wireless app, color change or audible sound.

Thus, personal health as monitored automatically may cause badge light circle to come on, flash or change color in any sequence. Also, patient behavior due to movement or medical monitoring may cause badge circle of light to come on; and generally any Soulyte-enabled device may monitor any vital signs, such as blood pressure, respiratory flow, hear beats, pulse, or any other medical monitoring procedure.

In charity application, one or more Soulyte-enabled badge may be worn for raising money and awareness by selling charitable brand or symbol to wear. Thus, Soulyte-enabled devices may be worn to display charity symbol/color to show personal/cause support; and if person already has Soulyte-enabled device, then they can just buy/download the symbol for charity/cause.

Hence, with such charitable approach, linked app may determine automatically how much has been raised by particular person wearing Soulyte badge. Further, when person with Soulyte badge device scans barcode or knocks badge with smartphone, they automatically donate to charitable cause, for example, by getting link to video to view sponsored by brand.

It is contemplated further that such charitable activity may automatically connect Soulyte-enabled device/service remotely to one or more social media network, such as Facebook, Snapchat, Twitter, Pinterest, YouTube, Instagram, etc., e.g., accordingly to show followers, tweets, or any other measurement of engagement, such as showing color on Soulyte badge or circle of color, as well as electronic device flashing, sounding noise when interaction takes place on social media, or if badge screen changes at all through social media interaction.

In fashion application, one or more Soulyte-enabled badge may be configured automatically to show support for brand/cause, e.g., by providing coupon/incentive for next wearable merchandise/service purchase. Such device may be embedded into garment/material so that it shows brand name, cause supported, and/or link to controller app; such Soulyte-enabled device can also be tapped by another person phone to give to that cause and get promotional voucher to buy that brand product. Optionally, Soulyte-enabled functionality may be embedded or condensed onto a small chip. Generally, it is contemplated that brand or organization uses Soulyte badge screen to show logo embedded in clothes, or circle of light shows cause related engagement from brand, or otherwise flashes or gives sound. Additionally, it is contemplated that Soulyte tracking software may be activated by phone tap of NFC; or link is provided by barcode scan or NFC bump on the device.

In pet-monitoring application, one or more Soulyte-enabled badge may be attached to dog collar and used to track where pet is at any one time, for example, by using GPS tracking module; optionally, badge screen can show name, address and phone number of pet owner. Generally, it is contemplated that such badge may display circle of color on pet device automatically, or show company logo or cause on screen, as well as track pet movement.

Generally, regarding Soulyte-enabled device and/or method, it is contemplated that sequence of color may be generated programmably in particular patterns, e.g., circle, to denote personalizable attributes variously: social media engagement, i.e., number of followers, tweets, etc.; level of giving or donation; level of attainment/rank/points/management/etc.; level of health, i.e., derived from monitors; level of mood; level of happiness; item or thing within area or not (e.g., pet); musical note or set of notes in certain pattern; song or set of songs; sport team; sports event, e.g., goal or touch down; music group or band; signal from controller; pressure level; location; time; alarm; voice; voice-activated software; motion or movement; submersion in any liquid; gas detection; liquid detection; and/or shopping event or offer, etc.

In an embodiment of the invention, sample Soulyte-enabled display image features of wearable personal wireless/Bluetooth badge, smart device, or other similarly functional wireless electronic apparatus shows programmably sequential color illumination LCD/LED devices (white/red/orange/yellow/green/light-blue/dark-blue/purple/etc.) arranged in circle for rotational direction clockwise/counter-clockwise preferably using flashing lights, around touch-sensitive screen that may include badge wearer unique barcode and/or logo of supporting brand. It is contemplated generally herein that Soulyte-enabled apparatus comprises functionally integrated one or more opto/mechanical/electrical sensors, multi-media audio/visual interfaces, controller/processor units, wireless communication devices, as well various software and/or firmware configured programmably using one or more web/wireless application programs according to one or more attributes described herein.

In an embodiment of the invention, Application Program Interface (API) for Soulyte-enabled apparatus and/or method contemplated various parameters programmably including, but not limited to: color to outside ring, color to inside ring, image to screen, video to screen, unique linear barcode to screen, unique QR barcode, timing data, sound to speaker data, flashing signal timer, temperature data, GPS data, social media data, brightness, tone, etc. It is contemplated generally herein that Soulyte-enabled apparatus. It is contemplated generally herein that Soulyte-enabled badge, smartphone, and/or other wirelessly programmable apparatus having processor/controller, memory, user interface, network interface, etc. operates software/firmware/etc preferably according to such API.

In an embodiment of the invention, Soulyte-enabled badge device embodiment design is shown as representative sample, preferably configured in circular disk or cylindrical shape with 5 cm diameter, with 1 cm thickness, having a magnifying domed glass display or other clear screen 2 mm high, and magnetic and/or other attaching clip portion to secure device against garment material or other tissue fabric. It is contemplated alternatively that such device design may be shaped having other various non-circular shape or rectilinear portions, for example, including one or more digital processor/controller, accessible memory/storage, wireless communication interface, audio/visual media interface, power source, etc. Additionally, another embodiment design shows representative sample of badge dimensions operate-able with battery charger cradle.

In an embodiment of the invention, Soulyte-enabling computer application programs and/or equivalent hardware/software/firmware functionality is installed, downloaded, provided, or otherwise accessible by one or more wireless network device, such as interactive badge, smartphone, etc. Hence, one or more such device may access Soulyte-enabled data dashboard or other interface display according to such programs, for example, to transmit automatically via Bluetooth wireless protocol to one or more interactive badge device for personalized operation, as contemplated herein.

In an embodiment of the invention, representative functionality of one or more software module is shown interactively between wireless devices, for example, transmitted wirelessly via Bluetooth from one Soulyte-enabled device to another Soulyte-enabled device. As shown, here particularly badge controller software module automatically collects data initially from software application or wearable device, such as watch or sensor; then data may be input by web app user; then data may be input by administrator or any other source; then data formatted for transmission via Bluetooth or other wireless communication protocol; and the data may be transmitted via Bluetooth or other radio frequency system to badge or other wireless device. Also, transmitted and/or processed data may then be displayed as: color based on data value, time, movement, temperature, sound level/frequency or location; color flashes at different frequencies based on data value, time, movement, temperature, sound level/frequency or location; image and video based on data value, time movement, temperature, sound level/frequency or location; barcode based on data value, time movement, temperature, sound level/frequency or location; and/or sound speaker based on data value, time movement, temperature, sound level/frequency or location.

In an embodiment of the invention, alternate embodiment of Soulyte-enabled system, process, and/or wireless device assembly contemplates optional light-scanning, detection or equivalent recognition functionality, for example, having smartphone badge light scanning sensor and/or software that picks up color of interactive badge, and may display content or link associated with such detected badge color. Furthermore, re FIG. 7, alternate embodiment of Soulyte-enabled system, process, and/or wireless device assembly contemplates optional light-scanning, detection or equivalent recognition functionality, having smartphone badge light scanning sensor and/or software that picks up color and/or barcode or other identifying pattern of interactive badge, and may display content or link associated with such detected badge color.

In an embodiment of the invention, Soulyte-enabled system may further include badge processing according to app software (i.e., LiikeMinded) that effectively serves to unite charitable organization/cause/interest, for example, using one or more sponsoring brand and advocates accordingly for such cause. In this charitable application, such system effectively serves to unite participating people already campaigning for charitable cause to join team, and also trigger donations from engagement created socially, wirelessly and technically. Hence, as shown, system initially brand supplies approved assets automatically telling storey of support for cause; then advocates may share and promote content to followers, for free; then various follower interaction with content automatically triggers donation to charity; and comprehensive measurement and attribution of reach and impact may be reported to interested parties.

In an embodiment of the invention, in accordance with one or more embodiment of Soulyte-enabled system and/or method, various automated steps for user badge processing are illustrated operationally via flow chart, generally wherein user client device inputs into network database. Thus as shown initially for step-1, user downloads LiikeMinded app in accordance with Soulyte functionality on one or more wireless device; then login/registration for user device access; then user posts content on social network; then device app dashboard shows data; then information sent to Soulyte-enabled badge device; then Soulyte-enabled device displays data or color sequence; then image stays on until switched off; then power on image reappears.

In an embodiment of the invention, in accordance alternately with one or more embodiment of Soulyte-enabled system and/or method, various automated steps for user badge processing are illustrated operationally via flow chart, generally wherein user client device interacts to influence one or more Soulyte-enabled device. Thus as shown initially for step-2, user-A sees badge on user-B; then user-A downloads LiikeMinded app, then user orders Soulyte-enabled badge, and user-A logins to LiikeMinded app; then user-A scans barcode on badge; then user-A goes to link; then user-A reviews content; then user-A posts content on social media; and then user-A Soulyte-enabled badge shows activity.

Additionally, in accordance with one or more embodiment of Soulyte-enabled system and/or method, various automated steps for user badge processing are illustrated operationally via process overview that combines step-1 user-A Soulyte automated processing and step-2 user-A bonding with user-B to form associated soulmate.

Thus, as shown initially per step-1, user-A having LiikeMinded app and wearing Soulyte-enabled device posts using LiikeMinded app; and then user-A changes color based on online views.

Next, as shown per step-2, user-A having LiikeMinded app and wearing Soulyte-enabled device scans user-B Soulyte-enabled device; then user-B having LiikeMinded app and wearing Soulyte-enabled device interacts accordingly with user-A to bond for forming soulmate; then user-A device changes color based on user-A scan of user-B Soulyte-enabled device, and thereby click content to user-B; and then user-B device changes color based on user-A scan to participate in charity/cause.

Therefore, it is contemplated herein generally that one or more interactive wireless device and/or software program is configured programmably, for example, whereby Soulyte app running on smartphone may control Soulyte-enabled badge, preferably using personalized interface that functionally accesses various programs, such as LiikeMinded app, any app carrying Soulyte libraries, any other device via Soulyte API, any location via Soulyte app, Soulyte commercial online site or shop with various charitable/cause logos and other sale-able images/logos, and Soulyte ads network for payment to show ads on badge, personal soul site for mood behavior app.

Furthermore, during Soulyte wireless network system operation interactively, it contemplated herein generally that one or more interactive wireless device and/or software program is configured programmably, for example, whereby Soulyte app running on smartphone may control Soulyte-enabled badge, such that one or more interacting person views badge, running Soulyte app, touching badge with smartphone, and one or more interactions occurs automatically; similarly same such interactions may occur when one or more person runs different app integrated with Soulyte configuration, i.e., SDL/libraries/etc. Optionally, one or more link may be transmitted wirelessly, e.g., NFC protocol, between Soulyte badge and viewer smartphone; such link initially may serve for joining LiikeMinded campaign, but may also serve as link from any Soulyte app displaying on badge.

In an embodiment of the invention, Soulyte-enabled system in one or more embodiment automatically configures controller, data fields, and/or API for enabling interactive data transfer between LiikeMinded app and Soulyte badge. Thus, as shown, social networking service, such as Facebook/twitter/Instagram/snapchat/etc. couples access functionally via universal API to Soulyte app having automated programmable controller/processor module and unique barcode generator, which may couple access functionally to fundraising campaign data via LiikeMinded web app/link. Then, such Soulyte app may be configured thereby to transmit to one or more badge various signaling, for example, such as image, video, ring colors, flash timer, barcode, brightness, length of time of display, on power on image reappears, etc.

In an embodiment of the invention, show various Soulyte interfaces with transmitted displays correspondingly.

Hence, generally, it is contemplated herein that so-called Soulyte device/system as well as automated method beneficially facilitates improved interpersonal communication. In particular, such improved approach effectively addresses the common problem of smartphone users increasingly failing to communicate directly with one another, i.e., by preferring to look at their phone screens constantly and instead interact more impersonally with them via wireless smartphone communication. Accordingly, Soulyte apparatus/process delivers a solution to this problem by providing effectively a catalyst to verbal communication. Thus, as described herein, Soulyte may serve as an extension to smartphone functionality in form of wearable interactive badge which displays user status, feelings, activity, desires, donations, needs or likes to the outside world, thereby allowing people to interact accordingly.

Therefore, Soulyte embodies a personal digital display, attached to clothes like badge, which displays information from multiple sources. Such information may be controlled automatically via Soulyte App connected to Soulyte device via Bluetooth or other wireless protocol. For example, Soulyte App controls what is displayed on Soulyte device, such as:

Donation level—Amount raised via Just Giving, Go fund me, LiikeMinded displayed in a number of ways including color and figures;

Location—Information broadcast through Soulyte App in particular location such as concert or sports event;

Social Media—Several parameters from popular social network sites can be displayed such as number of views, likes, friends, followers, etc.;

Commercial images and videos—Emblems can be purchased to support charities, such as pink ribbons and poppies;

Bluetooth Device—Data from Bluetooth device, such as fitness monitor or medical device can be displayed;

Adverts—Owners can run advertisements on Soulyte to earn revenue;

Any App with Soulyte Library—Soulyte library may provide developer to build direct links to Soulyte badge;

Your own information—Soulyte App allows wearer to control display directly allowing images and video to be displayed.

During operational interaction in one or more embodiment as described herein, Soulyte communicates using wireless protocol such as Near Field Communication, thereby allowing other users who are also running the Soulyte App to interact with the Soulyte by bringing their smartphone into close proximity of such badge device. Accordingly, such feature may enable others to obtain links from Soulyte, such as joining fundraising programs being displayed or media downloads such as music tracks, videos or offer coupons.

Therefore, advantageously, Soulyte apparatus/method satisfies various purposes, i.e., that serve different attractions for different people. One Soulyte application automates fundraising, for example, whereby Soulyte replaces Poppy or Ribbon as symbol of support for cause.

Optionally, Soulyte may change display of symbol, accordingly for use to raise money through interactive link.

Another Soulyte application automates connection to social media site, such as Facebook or Twitter, thereby enabling wearer of badge to display status as available and/or number of followers, friends, and sharers, etc. Alternatively, Soulyte application may appear when one or more development libraries are integrated into their apps providing direct link to Soulyte Badge.

Foregoing descriptions of specific embodiments of the invention have been presented for purposes of illustration and description. They are not intended to be exhaustive or to limit the invention to the precise forms disclosed. Modifications and variations are possible in light of the above teaching. The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

I claim:

1. A method for color and symbol-coded signaling a first users personal attribute from a first users digital badge device in a line of sight of a different user, said method comprising the steps of:
    configuring a first user digital badge device to interact wirelessly with a first user mobile device, wherein the first user digital badge device comprises a housing further configured without a strap and with a display screen to be worn on a chest of the first user in a line of sight of the different user;
    determining at least one personal attribute of the first user, wherein the personal attribute is at least one of the first users' affiliation or supported cause, emotional, mental, or physical state, age compliance, or physical activity status, and wherein the determination is based on an input of the first user or a device-captured input of the first user; and
    outputting a pre-defined color and/or symbol code on the display screen of the first users interactive badge device for line-of-sight display to the different user, wherein the pre-defined color and/or symbol-coded display is based on at least one of the first users input or first users device-captured input through the first user mobile device, and wherein the color and/or symbol code displayed represents a specific pre-defined personal attribute of the first user for line-of-sight display to the different user.

2. The method of claim 1, wherein the color and symbol-coded signaling of a first users personal attribute is at least one of a colored circle, square, or triangle.

3. The method of claim 1, wherein the personal attributes are at least one of a personal mood, medical condition, physical movement, age, personal availability, cause, or relaxation attribute.

4. The method of claim 1, wherein the first user input is a user selection from a choice of personal attributes through the first user mobile device application interface.

5. The method of claim 1, wherein the first user device captured input is derived from any one of a sensor reading from a wearable or IoT device.

6. The method of claim 1, further comprising a second user badge device worn by a second user, wherein the second user badge device is configured for accepting or declining an approach or digital interaction from the first user.

7. The method of claim 6, wherein the accepting or declining by the second user or second user badge device is based on decoding a tag sent from the first user badge device.

8. The method of claim 7, wherein the decoding is based on matching of outwardly displayed color and symbols on each of the badge devices.

9. The method of claim 1, further comprising a digital event or interaction between the first user badge device and second user badge device, wherein the event or interaction is the transfer of at least one of an image, video, sound, vibration, flash, signal, symbol, color, text, sequence, upload, download from the first users digital badge device, mobile device, or over a network.

10. A device for color and symbol-coded signaling a first users personal attribute in a line of sight of at least a second user, said device comprising:
    a housing;
    said housing configured without a strap and to be worn on a chest of a first user, further comprising a display for line-of-sight display to any user not the first and further comprising an interface for wirelessly interacting with a mobile device of the first user;
    determining at least one personal attribute of the first user, wherein the personal attribute is at least one of the first users' affiliation or supported cause, emotional, mental, or physical state, age compliance, or physical activity status, and wherein the determination is based on an input of the first user or a device-captured input of the first user relayed through the first users mobile device and; and
    outputting a pre-defined color and/or symbol code on the display screen of the first users interactive badge device for line-of-sight display to at least the second user, wherein the pre-defined color and/or symbol-coded display is based on at least one of the first users input or first users device-captured input, and wherein the color and/or symbol code displayed represents a specific pre-defined personal attribute of the first user for line-of-sight display to at least the other user who is not the first user.

11. The method of claim 10, wherein the housing comprises a flying saucer design having a magnetic clip and a domed glass screen where the domed glass screen magnifies the LED display screen.

12. The method of claim 11, wherein the housing is circular, with a top face disposed with a center device display; a side wall disposed with a surround device display; and user controls disposed on any one of the top face and, or the side wall.

13. The method of claim 10, wherein the interface is configured to communicate via any one of a short-range communication protocol with at least one of a mobile device of the first user and, or the interactive badge device of at least the second user.

14. A system for wirelessly interacting a first users digital badge device with a second users digital badge device, said system comprising:
a first users digital badge device;
a second users digital badge device;
a processor;
a memory element with encoded instructions coupled to the processor, when implemented by said processor, configure the system to:
interact wirelessly a mobile device of the first and second user with the first and second users digital badge device respectively, wherein said first and second user digital badge devices are configured with a housing disposed without a strap and to be worn on a chest of a first user and second user, further comprising a display for line-of-sight display to the other user;
determine at least one personal attribute of the first user, wherein the personal attribute is at least one of the first users' affiliation or supported cause, emotional, mental, or physical state, age compliance, physical activity status, or availability for approach to initiate a digital interaction, and wherein the determination is based on an input of the first user or a device-captured input of the first user relayed through the first users mobile device;
outputting a pre-defined color and/or symbol code on the display screen of the first users interactive badge device for line-of-sight display to at least the second user, wherein the pre-defined color and/or symbol-coded display is based on at least one of the first users input or first users device-captured input, and wherein the color and/or symbol code displayed represents a specific pre-defined personal attribute of the first user for line-of-sight display to at least the second user; and
initiating a digital event or interaction between the first users digital badge device and the second users digital badge device, wherein the interaction comprises a transfer of a signal with a tag from the first users digital badge device to the second users digital badge device upon a matching of displayed color and symbol codes on each of the first and second users digital badge device, decoding the tag from the signal transferred from the first users digital badge device by the second users digital badge device, validating the signal and enabling the digital event to occur between digital badge devices.

15. The system of claim 14, wherein the digital event is the transfer of at least one of an image, video, sound, vibration, flash, signal, symbol, color, text, sequence, upload, download from the first users digital badge device, mobile device, or over a network.

16. The system of claim 15, wherein image or video is a curated line of static, dynamic, and, or scheduled images and, or video.

17. The system of claim 14, further comprising an advertising platform, wherein advertisers target users for content display based on activity of the first user.

18. The system of claim 14, further comprising a bidding module, wherein an advertiser bids among other advertisers for engaging the first user for incorporating a winning bid advertisement into the display of said first user.

19. The system of claim 14, further comprising a store platform, wherein the first user may purchase digital downloads of content for first user badge display.

20. The system of claim 14, further comprising a distributive digital ledger, wherein each exchange among any user is represented as a unique node in the digital ledger, said node tagged with meta data facilitating at least one of a transaction, validation and, or registration for each exchange.

* * * * *